United States Patent [19]

Friedrich et al.

[11] Patent Number: 5,827,731
[45] Date of Patent: Oct. 27, 1998

[54] THROMBIN-INHIBITORY PROTEIN FROM TICKS

[75] Inventors: Thomas Friedrich, Darmstadt; Siegfried Bialojan, Oftersheim; Claus Bollschweiler, Heidelberg; Christoph Kuenast, Otterstadt, all of Germany

[73] Assignee: BASF Aktiengesellschaft, Ludwigshafen, Germany

[21] Appl. No.: 859,183

[22] Filed: May 20, 1997

Related U.S. Application Data

[63] Continuation of Ser. No. 415,999, Apr. 4, 1995, abandoned, which is a continuation of Ser. No. 204,244, Mar. 8, 1994, abandoned.

[30] Foreign Application Priority Data

Oct. 22, 1991 [DE] Germany .................... 41 34 814.1

[51] Int. Cl.⁶ .................... C07K 14/435; C07K 14/81; C12N 15/15; A61K 38/57
[52] U.S. Cl. .................... 435/320.1; 435/69.2; 514/12; 514/822; 530/324; 536/23.5
[58] Field of Search .................... 435/69.2, 214, 435/320.1; 514/12, 822; 530/300, 324, 858; 536/23.5

[56] References Cited

FOREIGN PATENT DOCUMENTS

WO 19/04275   9/1990   WIPO .

OTHER PUBLICATIONS

Characterization of Recombinant Tick Antiocoagulant Peptide, Neepert et al. J. of Biological Chemistry, 265, 17746–17752 (1990).

*Primary Examiner*—Dian C. Jacobson
*Attorney, Agent, or Firm*—Keil & Weinkauf

[57] ABSTRACT

A novel thrombin-inhibitory protein from ticks with a molecular weight of about 8000 Dalton and the N terminus Leu-Asn-Val-Leu-Cys-Asn-Asn-Pro-His-Thr-Ala-Asp-Cys-Asn-Asn-Asp-Ala-Gln-Val-Asp is described. The protein is suitable for controlling diseases.

6 Claims, No Drawings

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 33 amino acids
        ( B ) TYPE: amino acid
        ( D ) TOPOLOGY: linear ( x i ) SEQUENCE DESCRIPTION: SEQ ID NO: 1:

Leu Asn Val Leu Cys Asn Asn Pro His Thr Ala Asp Cys Asn Asn Asp
 1               5                    10                  15

Ala Gln Val Asp Arg Tyr Phe Arg Glu Gly Thr Thr Cys Leu Met Ser
              20                  25                  30

Pro ( 2 ) INFORMATION FOR SEQ ID NO: 2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

TGYAAYAAYC CNCAYACNGC                                                        20

( 2 ) INFORMATION FOR SEQ ID NO: 3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CCNCAYACNG CNGAYTGYAA                                                       20

( 2 ) INFORMATION FOR SEQ ID NO: 4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

TTGAATGTGT TGTCCAATAA TCCGCATACG GCCGATTGCA AC                    42

( 2 ) INFORMATION FOR SEQ ID NO: 5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GGGGGGGTCG ACGTGCTAGT ACCTTACATG TTT                               33

( 2 ) INFORMATION FOR SEQ ID NO: 6:

( i ) SEQUENCE CHARACTERISTICS:
   ( A ) LENGTH: 291 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 6:

```
TTG  AAT  GTG  TTG  TGC  AAT  AAT  CCG  CAT  ACG  GCC  GAT  TGC  AAC  AAT  GAT        48
Leu  Asn  Val  Leu  Cys  Asn  Asn  Pro  His  Thr  Ala  Asp  Cys  Asn  Asn  Asp
 1              5                        10                       15

GCA  CAG  GTT  GAC  AGA  TAT  TTT  AGG  GAG  GGG  ACA  ACG  TGC  CTA  ATG  TCC        96
Ala  Gln  Val  Asp  Arg  Tyr  Phe  Arg  Glu  Gly  Thr  Thr  Cys  Leu  Met  Ser
               20                        25                       30

CCA  GCA  TGC  ACG  AGC  GAA  GGA  TAC  GCC  TCT  CAG  CAC  GAA  TGT  CTC  AGG       144
Pro  Ala  Cys  Thr  Ser  Glu  Gly  Tyr  Ala  Ser  Gln  His  Glu  Cys  Leu  Arg
          35                        40                       45

CCT  GCT  TTG  TTG  GCG  GGG  AAG  ACC  ACA  GCA  GTG  AAA  TGC  ACA  GCT  CAT       192
Pro  Ala  Leu  Leu  Ala  Gly  Lys  Thr  Thr  Ala  Val  Lys  Cys  Thr  Ala  His
     50                        55                       60

GCC  TTG  GTG  ACC  CGC  CCA  CTT  CCT  GCG  CGG  AAG  GCA  CGG  ACA  TCA  CCT       240
Ala  Leu  Val  Thr  Arg  Pro  Leu  Pro  Ala  Arg  Lys  Ala  Arg  Thr  Ser  Pro
 65                       70                       75                       80

ACT  ACG  ATT  CTG  ATA  GCA  AAA  CAT  GTA  AGG  TAC  TAGCAGGTCG  ACCCCCCC          291
Thr  Thr  Ile  Leu  Ile  Ala  Lys  His  Val  Arg  Tyr
                    85                       90
```

( 2 ) INFORMATION FOR SEQ ID NO: 7:

( i ) SEQUENCE CHARACTERISTICS:
     ( A ) LENGTH: 91 amino acids
     ( B ) TYPE: amino acid
     ( D ) TOPOLOGY: linear ( x i ) SEQUENCE DESCRIPTION: SEQ ID NO: 7:

```
Leu  Asn  Val  Leu  Cys  Asn  Asn  Pro  His  Thr  Ala  Asp  Cys  Asn  Asn  Asp
 1              5                        10                       15

Ala  Gln  Val  Asp  Arg  Tyr  Phe  Arg  Glu  Gly  Thr  Thr  Cys  Leu  Met  Ser
               20                        25                       30

Pro  Ala  Cys  Thr  Ser  Glu  Gly  Tyr  Ala  Ser  Gln  His  Glu  Cys  Leu  Arg
          35                        40                       45

Pro  Ala  Leu  Leu  Ala  Gly  Lys  Thr  Thr  Ala  Val  Lys  Cys  Thr  Ala  His
     50                        55                       60

Ala  Leu  Val  Thr  Arg  Pro  Leu  Pro  Ala  Arg  Lys  Ala  Arg  Thr  Ser  Pro
 65                       70                       75                       80

Thr  Thr  Ile  Leu  Ile  Ala  Lys  His  Val  Arg  Tyr
                    85                       90
```

( 2 ) INFORMATION FOR SEQ ID NO: 8:

( i ) SEQUENCE CHARACTERISTICS:
     ( A ) LENGTH: 14 amino acids
     ( B ) TYPE: amino acid
     ( D ) TOPOLOGY: linear ( x i ) SEQUENCE DESCRIPTION: SEQ ID NO: 8:

```
Ser  Asp  Tyr  Glu  Phe  Pro  Pro  Pro  Lys  Lys  Xaa  Arg  Pro  Gly
 1              5                        10
```

( 2 ) INFORMATION FOR SEQ ID NO: 9:

( i ) SEQUENCE CHARACTERISTICS:
     ( A ) LENGTH: 7 amino acids
     ( B ) TYPE: amino acid
     ( D ) TOPOLOGY: linear ( x i ) SEQUENCE DESCRIPTION: SEQ ID NO: 9:

Cys Asn Asn Pro His Thr Ala
 1               5

( 2 ) INFORMATION FOR SEQ ID NO: 10:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO: 10:

Pro His Thr Ala Asp Cys Asn
 1               5

( 2 ) INFORMATION FOR SEQ ID NO: 11:

( i ) SEQUENCE CHARACTERISTICS:
        ( A ) LENGTH: 20 amino acids
        ( B ) TYPE: amino acid
        ( D ) TOPOLOGY: linear ( x i ) SEQUENCE DESCRIPTION: SEQ ID NO: 11:

Leu Asn Val Leu Cys Asn Asn Pro His Thr Ala Asp Cys Asn Asn Asp
 1               5                   10                  15

Ala Gln Val Asp
             20

THROMBIN-INHIBITORY PROTEIN FROM TICKS

This application is a continuation of application Ser. No. 08/415,999, filed on Apr. 4, 1995, now abandoned, which is a continuation of application Ser. No. 08/204,244, filed on Mar. 8, 1994 now abandoned.

The present invention relates to a novel thrombin-inhibitory protein from ticks and a process for preparing it.

Thrombin inhibitors are important therapeutic substances used, for example, for the prophylaxis or treatment of thromboses or arterial reocclusions.

German Offenlegungsschrift DE 39 31 839 describes a thrombin inhibitor isolated from the argasid tick Ornithodoros moubata. This protein has a molecular weight of about 15,000 Dalton, an isoelectric point at pH 4–5 and the N-terminal amino-acid sequence SDYEFPPPKKXRPG (SEQ I.D. NO: 8).

European Published Application EP 345 614 describes the thrombin-inhibitory agent amblyommin which is isolated from bont ticks. This is a protein with a molecular weight of 20,000–30,000 Dalton and an isoelectric point of 5.05–5.65.

However, to date, no protein with a thrombin-inhibitory action has been found to be suitable as drug in terms of high activity, lack of antigenicity, long biological half-life, and few side effects, such as risk of hemorrhage.

It is an object of the present invention to provide novel thrombin inhibitors which are suitable as drugs on the basis of the abovementioned properties.

We have found that this object is achieved by a novel thrombin-inhibitory protein isolated from ticks.

The novel protein has the following physicochemical properties. Molecular sieve chromatography reveals that it has a molecular weight of 22,000–28,000 Dalton. A molecular weight of 8000±1500 Dalton is determined in an SDS polyacrylamide gel. Determination of the isoelectric point reveals that it is at a pH below 3.8.

The protein binds specifically to a thrombin affinity column. It inhibits the biological activity of thrombin in an in vitro enzyme assay.

Silver staining of the protein band in a polyacrylamide gel is not possible; it is visible only as an unstained spot on a stained background.

The following N-terminal amino-acid sequence was determined for the protein (SEQ ID NO: 1):

with a precipitant, preferably trichloroacetic acid, and subsequently removing them.

Further purification of the protein is possible by chromatographic methods, preferably ion exchange chromatography and/or affinity chromatography. A purification step by thrombin affinity chromatography is particularly preferred.

The purification of the protein can be monitored by a thrombin activity assay. It is expedient to use for this an optical assay in which a chromogenic substrate, for example Chromozym T, is converted by thrombin. The fractions containing the novel protein can be identified by their thrombin-inhibiting action on addition to this optical assay.

Genetic engineering methods are particularly suitable for preparing the protein according to the invention.

To do this, a cDNA gene bank from the tick is constructed in a conventional manner. It is possible to isolate the gene coding for the protein according to the invention from this gene bank by, for example, preparing a DNA probe whose sequence is obtained from the N-terminal amino-acid sequence described above by translation back using the genetic code. The appropriate gene can be found and isolated by hybridization with this DNA probe.

However, it is also possible to employ the polymerase chain reaction (PCR) technique to prepare the appropriate gene. For example, a primer whose sequence has been obtained by translation back from the N-terminal amino-acid sequence described above, and a second primer whose sequence is complementary to the 3' end of the cDNA gene fragment, preferably with the sequence poly(dT), can be used to prepare the cDNA gene fragment for the protein according to the invention by the PCR technique. The appropriate gene can also be isolated by constructing an expression gene bank from ticks and screening this with an antibody directed against the protein according to the invention.

The gene for the protein described in the introduction has the nucleotide sequence depicted in SEQ ID NO: 6.

Apart from this gene, other suitable nucleotide sequences are those which code for the amino-acid sequence depicted in SEQ ID NO: 7 but which, as a consequence of the degeneracy of the genetic code, have a nucleotide sequence differing from SEQ ID NO: 6. Genes of this type can be prepared by total chemical synthesis or by mutagenesis of the SEQ ID NO: 6 nucleotide sequence.

Once the appropriate gene has been isolated, it can be expressed by genetic engineering methods in organisms, eg. in bacteria, yeasts, eukaryotic cells, with the aid of an Leu—Asn—Val—Leu—Cys—Asn—Asn—Pro—His—Thr—Ala—Asp—Cys—Asn—
Asn—Asp—Ala—Gln—Val—Asp—Arg—Tyr—Phe—Arg—Glu—Gly—Thr—Thr—
Cys—Leu—Met—Ser—Pro.

The complete amino acid sequence of the novel protein is depicted in SEQ ID NO: 7.

Other proteins according to the invention are those which differ from the amino-acid sequence depicted in SEQ ID NO: 7 by replacement of up to 10 amino acids or deletion of individual amino acids.

Amino-acid sequences of these types can easily be prepared, for example, by genetic engineering via an appropriately mutated gene.

The novel protein can be isolated from ticks of the genus Ornithodoros. To do this, the ticks are homogenized, expediently in a buffer at pH 6–9, preferably pH 7–8, with a homogenizer, preferably a mixer. The insoluble constituents are then removed, preferably by centrifugation.

The protein can be further purified from the resulting solution by precipitating other proteins from the solution expression vector in a conventional manner. Preferably used are prokaryotes such as E. coli, and vectors with high-level expression, eg. under the control of the inducible tac promoter as present eg. in the plasmid pMAL-p2 (Protein Fusion and Purification System, GeneExpress; New England Biolabs). This results in periplasmic expression of a fusion protein comprising the maltose binding protein and the described thrombin inhibitor. The fusion partner can be deleted enzymatically after purification. The protein can be isolated from these recombinant host systems on the basis of the physicochemical properties described above.

The general procedure for the preparation by genetic engineering of a novel protein when the partial amino-acid sequence is known is described in textbooks of genetic engineering, for example E. L. Winnacker, Gene und Klone, Verlag Chemie, Weinheim, 1984. The experimental conditions for the individual methods, such as construction of a gene bank, hybridization and expression of a gene are described in J. Sambrook et al., Molecular Cloning, Cold Spring Harbor Laboratory, 1989.

The protein according to the invention is preferably used in the form of its pharmaceutically acceptable salts.

The novel protein has anticoagulant properties. It can be used, for example, for the prophylaxis of thromboses or arterial reocclusions, for the treatment of thromboses, for conserving blood or in extracorporeal circulations.

The invention is further illustrated by the following examples.

EXAMPLE 1

Purification of the Thrombin-Inhibitory Protein from Ticks

A laboratory culture of the ticks (Ornithodoros moubata) was maintained at 28° C. and 80% relative humidity. The ticks were allowed to feed off rabbits at 14-day intervals. Ticks in all stages of development were frozen at −20° C.

60 g of ticks were homogenized with 400 ml of 20 mM phosphate buffer, 150 mM NaCl (pH 7.5). The homogenate was centrifuged at 7000 rpm (Sorvall RC-5B, rotor GS-3) for 15 minutes. The precipitate was discarded, and 25 ml of 50% by weight trichloroacetic acid was added to the supernatant dropwise over a period of 15 minutes.

The mixture was then centrifuged (20 minutes, 7000 rpm) and the supernatant was neutralized with sodium hydroxide solution.

The neutralized supernatant was introduced into the dialysis tubing (exclusion volume 300 Da) and dialyzed several times against 10 times the volume of 20 mM sodium phosphate, 150 mM NaCl, pH 8.0.

The dialyzed protein solution was loaded onto a Q-Sepharose® column (Pharmacia) (60 ml/h) equilibrated with 20 mM sodium phosphate buffer pH 8.0 (diameter 1.5 cm, height 6 cm, volume 11 ml).

The column was washed with 10 column volumes of equilibration buffer.

Then a linear gradient from 50 ml of 20 mM sodium phosphate (pH 8.0) to 50 ml of 20 mM sodium phosphate (pH 8.0), 1M NaCl was applied.

Active fractions (measured by thrombin inhibitions) were collected.

The combined active fractions from the Q-Sepharose® chromatography were loaded onto a copper chelate chromatography column (diameter 2.5 cm, height 6 cm, volume 30 ml) equilibrated with 20 mM sodium phosphate (pH 8.0), 150 mM NaCl. The column was washed with 10 column volumes of equilibration buffer (1.5 ml/min) and eluted with a gradient from 150 ml of 20 mM sodium phosphate (pH 8.0), 150 mM NaCl to 150 ml of 20 mM sodium phosphate (pH 8.0), 150 mM NaCl, 100 mM imidazole.

Active fractions (measured by thrombin inhibition) were collected.

The combined active fractions were loaded onto an affinity column with immobilized thrombin (diameter 1.5 cm, height 6.5 cm, volume 11.5 ml, 60 ml/h). The column was prepared as described in Example 3.

The column was equilibrated with 20 mM sodium phosphate pH 7.5. After the protein solution had been loaded onto the column it was washed with 10 column volumes of equilibration buffer until the absorption at 280 nm decreased to zero.

It was then washed with 0.5M NaCl, 20 mM sodium phosphate buffer pH 7.5. This removed non-specifically adsorbed material.

Protein specifically bound to thrombin was eluted with 0.1M glycine, 0.5M NaCl pH 2.8. The column was then immediately readjusted to pH 7.5 with phosphate buffer.

The individual fractions were neutralized with 0.1M NaOH and tested for their inhibitory action on thrombin.

The fractions eluted by glycine/NaCl buffer pH 2.8 had a thrombin-inhibiting action.

The collected active fractions were, after neutralization, diluted with water (1:10) and loaded onto a Mono-Q® column (Pharmacia, volume 1 ml).

The column was equilibrated with 20 mM sodium phosphate buffer pH 7.5, 150 mM NaCl (buffer A). It was washed with buffer A until the absorption decreased to zero (10 minutes). The buffer was then changed over the course of 50 minutes to 20 mM sodium phosphate, pH 7.5, 800 mM NaCl (buffer B) (flow rate 0.5 ml/min).

Thrombin-inhibiting fractions were collected.

The collected fractions were further purified on an RP 318® (Biorad) HPLC column. The column was equilibrated with 0.1% by weight trifluoroacetic acid (TFA) in distilled water. The combined active fractions were loaded onto the column which was then eluted with a gradient to 0.1% TFA, 100% acetonitrile and a flow rate of 1 ml/min over the course of 1 hour. The absorption was determined at 280 nm, and 0.5 ml fractions were collected. The collected fractions were concentrated to dryness and taken up in phosphate-buffered saline (PBS) (0.8 g/l NaCl; 0.2 g/l HCl; 0.144 g/l sodium phosphate; 0.2 g/l calcium phosphate, pH 7.5) and the inhibitory activity was determined.

The protein was determined by the method of Bradford (Anal. Biochem., 72, (1976) 248–254) using bovine serum albumin (Boehringer Mannheim) as standard protein.

EXAMPLE 2

Determination of the Inhibition of Thrombin by the Inhibitor

Thrombin (Boehringer Mannheim) was dissolved to a final concentration of 25 mU/ml in phosphate buffered saline.

Chromozym TH (Boehringer Mannheim) was dissolved in 20 ml of $H_2O$ per vial.

50 μl of thrombin solution and 100 μl of Chromozym and 25 μl of sample or buffer were placed in the wells of a microtiter plate. The absorption at 405 nm was measured at 37° C. immediately thereafter at time 0 and after 30 minutes.

When the sample was deeply colored another control without thrombin was treated as described above.

The activity of thrombin liberates a dye which absorbs at 405 nm from the chromogenic substrate. Inhibition of the thrombin by an inhibitor is evident from a smaller increase in absorption at 405 nm and was quantified using a calibration plot.

EXAMPLE 3

Preparation of an Affinity Column with Thrombin as Ligand a) Coupling:
  2 g of CNBr-activated Sepharose (Pharmacia) were washed with 200 ml of 1 mM HCl on a suction funnel.

The gel was taken up in 100 mM NaHCO₃, 500 mM NaCl pH 8.3 and immediately mixed with 10,000 units of thrombin (Sigma) in 100 mM NaHCO₃, 500 mM NaCl, pH 8.3.

The solution was gently shaken at 4° C. for 24 hours.

b) Blocking:

The gel material was allowed to settle and then washed with 100 mM NaHCO₃, 500 mM NaCl, pH 8.3. The Sepharose was then incubated with 100 mM NaHCO₃, 500 mM NaCl, 1M ethanolamine pH 8.3 for 2 hours.

c) Preparation:

To remove unbound thrombin, before use the gel material is washed once more in the column with 20 column volumes of PBS pH 7.4.

EXAMPLE 4

Determination of the Molecular Weight by Molecular Sieve Chromatography

Material purified by Mono-Q® chromatography was passed at a flow rate of 1 ml/min in 20 mM sodium phosphate, 150 mM NaCl, pH 7.5 through a Spherogel® TSK 3000 SW molecular sieve column (Pharmacia, diameter 7.5 mm, height 60 cm).

The reference proteins were treated to the same procedure (serum albumin MW 67,000 Da, ovalbumin MW 45,000 Da, chymotrypsinogen A MW 25,000 Da).

The logarithm of the molecular weight of the reference proteins was plotted against their elution time.

The thrombin inhibition by the eluted fractions of the sample was determined.

The logarithm of the molecular weight of the inhibitor was obtained from the intercept of the elution time on the calibration line.

The molecular weight was found to be 22,000–28,000 Dalton.

EXAMPLE 5

Determination of the Molecular Weight by Tricine SDS Polyacrylamide Gel Electrophoresis (Reference: Analytical Biochemistry, 166, (1987) 368–379 Tricine-Sodium Dodecyl Sulfate-Polyacrylamide Gel Electrophoresis for the Separation of Proteins in the range from 1–1000 kDa, Schagger, H. and von Jagow, G.)

The gel electrophoresis was carried out as stated in the reference at 20 mA and 1400 V, 30 watt.

The molecular weight determined by this method was 8000±1500 Dalton.

The reference proteins were intact myoglobin 17.2 kDa, myoglobin I+II 14.6 kDa, myoglobin I 8.2 kDa, myoglobin II 6.4 kDa, myoglobin III 2.6 kDa and myoglobin 1–14.

EXAMPLE 6

Determination of the Sequence of the Inhibitor Reduction and Carboxymethylation 2.8 ml of protein solution (0.029 mg/ml) were mixed with 0.28 ml of buffer (1M tris/HCl, 0.5M guanidine hydrochloride, pH 8.6). Then 0.116 ml of dithiothreitol (DTT, 10 mg/ml) was added and the mixture was incubated at 37° C. for 10 minutes. After addition of 0.185 ml of iodoacetamide (10 mg/ml) the mixture was incubated at 37° C. for 90 minutes. The reaction was stopped with 0.073 ml of DTT as above.

The protein was purified by renewed reversed phase HPLC on RP 318®. The mixture was adjusted to a final concentration of 0.1% by weight trifluoroacetic acid (TFA) and separated in an HPLC system from Hewlett Packard (HP 1090 Liquid Chromatograph). The column was washed with solvent A (0.1% TFA, 100% H₂0) for 5 minutes. Then the proportion of solvent B (90% acetonitrile, 10% H₂O, 0.1% by weight TFA) was increased to 50% over the course of 120 minutes. The absorption of the eluate at 214 and 280 nm was measured. Absorbing fractions were collected. The protein was identified by SDS gel electrophoresis and subjected to sequence analysis in an applied biosystems 477 A protein sequencer in accordance with the manufacturer's instructions.

The following sequence was obtained (SEQ ID NO: 1):

Leu—Asn—Val—Leu—Cys—Asn—Asn—Pro—His—Thr—Ala—Asp—Cys—Asn—Asn—Asp—Ala—Gln—Val—Asp—Arg—Tyr—Phe—Arg—Glu—Gly—Thr—Cys—Leu—Met—Ser—Pro.

EXAMPLE 7

Determination of the Isoelectric Point by Isoelectric Focusing

The determination was carried out with an LKB Multiphor 2117 (Horizontal system) and an LKB 2103 power supply. Precast gels were employed (Pharmacia Ampholine PAGplate pH 3.5–9.5). The standard proteins employed were amyloglucosidase, pH 3.5; soybean trypsin inhibitor, pH 4.55; β-lactoglobulin A, pH 5.2; bovine carbonic anhydrase, pH 5.85; human carbonic anhydrase, pH 6.55; horse myoglobin, pH 6.85 and 7.35; lentil lectin, pH 8.15, 8.45, 8.65 and trypsinogen, pH 9.3.

Focusing conditions: 1500 volt, 30 watt.

Buffer: Anode 1M phosphoric acid Cathode 1M sodium hydroxide solution

The plates were prefocused for 30 minutes to produce a pH gradient. The samples were loaded onto filter disks which lay on the gel. Focusing was continued for 30 minutes, the filter disks were removed and, after a further 30 minutes, the focusing was stopped. The gels were immediately cut into 2 mm slices and transferred into distilled water. The protein eluted out of the gel slices overnight. The location of the thrombin inhibitor was determined by a thrombin inhibition assay. The pH can also be determined directly using a pH electrode. The reference substance hirudin had an isoelectric point of pH 3.5 and below. The novel inhibitor had an isoelectric point below pH 3.8.

EXAMPLE 8

Preparation of a DNA Sequence which Codes for a Thrombin-Inhibitory Protein a) Isolation of RNA and preparation of a cDNA bank Total RNA was obtained from whole animals of the species Ornithodoros moubata by disruption in guanidinium thiocyanate. This was done using the materials and according to the instructions in the RNA isolation kit from Stratagene, La Jolla, Calif., USA (Catalog No.: 200345).

The polyadenylated messenger RNA was selected from the total RNA by oligo(dT) affinity separation. This process was carried out with materials and according to the instructions in the PolyATtract mRNA isolation system from Promega, Madison, Wis., USA (Catalog No.: Z5200).

cDNA was synthesized from polyadenylated messenger RNA using the materials and according to the instructions in the ZAP-cDNA synthesis kit from Stratagene, La Jolla, Calif., USA (Catalog No.: 200400) and was then cloned into the Eco RV restriction site of the plasmid pBluescript II SK from Stratagene, La Jolla, USA (Catalog No.: 212205).

b) Preparation of oligonucleotide probes for the PCR

Peptides from the protein sequence described in Example 6 were used as basis for the cloning of cDNA fragments by the polymerase chain reaction (PCR, see Molecular Cloning, 2nd edition (1989), Sambrook, J. et al., CSH Press, page 14.1 et seq.).

On the basis of the genetic code it is possible to deduce the nucleic acid sequence (SEQ ID NO: 2):

5'-TGY AAY AAY CCN CAY ACN GC-3' from the peptide sequence I):

$NH_2$-Cys-Asn-Asn-Pro-His-Thr-Ala (Pos 5–11)   (SEQ ID NO: 9)

and the nucleic acid sequence (SEQ ID NO: 3):

5'-CCN CAY ACN GCN GAY TGY AA TG-3' from the peptide sequence II):

$NH_2$-Pro-His-Thr-Ala-Asp-Cys-Asn (Pos 8–14), (SEQ ID NO: 10)

each of the coding DNA strand. Because of the known degeneracy of the genetic code, a plurality of nucleotides (N: A, C, G, T; Y: C, T;) can be used at some positions. The complexity of the mixture is therefore 256-fold for SEQ ID NO: 2 and 512-fold for SEQ ID NO: 3. The said sequences were synthesized as oligonucleotides.

The syntheses were carried out with an Applied Biosystems type 360A DNA synthesizer. The oligonucleotides were purified, after removal of the protective groups, by gel electrophoresis on a polyacrylamide/urea gel.

c) PCRs and cloning of a part cDNA sequence

The polymerase chain reaction was carried out in accordance with known protocols (see Molecular Cloning, 2nd edition (1989), Sambrook, J. et al., CSH Press, page 14.1 et seq.). A Perkin-Elmer DNA thermal cycler was used for this. The principle of "internal" primers described by Frohmann, M. A. et al. (Proc. Natl. Acad. Sci. USA 85, (1988) 8998–9002, as modified by Fritz, J. D. et al. (Nucl. Acids Res. 19, (1991) 3747) was employed in this case.

Specifically, the cDNA from a) was amplified with 20 $\mu$mol each of the oligonucleotides SEQ ID NO: 2 and the synthetic T7 primer (derived from pBluescript II SK). The conditions for this were 95° C. for 1', 72° C. for 3' for 35 cycles.

The PCR products were fractionated by electrophoresis on a 1.2% LMP agarose TBE gel.

Five slices were cut out of the gel over the entire length of the "streak" and were melted as separate fractions with DNA fragments of increasing molecular mass.

Aliquots of these fractions were then used separately in a second PCR with 20 $\mu$mol of each of the oligonucleotides ii) and the synthetic M13–20 primer (derived from pBluescript II SK).

The agarose content never exceeded 1/10 of the volume of the PCR mixture. Reaction conditions: 95° C. for 1', 50° C. for 2', 72° C. for 3' for 35 cycles.

Fractionation by gel electrophoresis of the amplification products of these fractions clearly showed a reduction in the complex spectrum of products from the first PCR as far as a defined band after the second PCR.

The PCR products selected in this way were eluted by standard methods. Subcloning into the EcoRV cleavage site of the vector pBluescriptKS and multiplication of the plasmid in *E. coli* DH5alpha were followed by sequence analysis of a clone which showed an open reading frame of 91 amino acids (SEQ ID NO: 6) which agreed with the predicted protein sequence (SEQ ID NO: 1).

The DNA and the amino acid sequence derived therefrom are depicted in SEQ ID NO: 6.

d) Heterologous expression

The following oligonucleotides were synthesized for the heterologous expression of the sequence of 91 amino acids in *E. coli:*

Nucleic acid sequence SEQ ID NO: 4 and nucleic acid sequence SEQ ID NO: 5

SEQ ID NO: 4 is derived from SEQ ID NO: 1; it corresponds to the sequence for the amino acids in positions 1–14; SEQ ID NO: 5 is derived from SEQ ID NO: 6 and corresponds to the sequence of the complementary strand for amino acids 87–91 and the stop codon. The additional 15 nucleotides at the 5' end of SEQ ID NO: 5 are intended to reconstitute a Sal I cleavage site for cloning purposes.

A PCR with these two oligonucleotides and the DNA cloned in c) as template led to the isolation of a cDNA sequence which contains the complete coding region of the abovementioned thrombin inhibitor (SEQ ID NO: 6). The reaction conditions were 10 $\mu$l of template, 20 $\mu$mol each of oligonucleotides SEQ ID NO: 4 and SEQ ID NO: 5; 95° C. for 1', 55° C. for 2', 55° C. for 2', 72° C. for 3' for 35 cycles.

The PCR product was then cut with Sal I, analyzed by gel electrophoresis and eluted by standard methods.

For heterologous expression in *E. coli*, the PCR fragment was subcloned into the inducible vector which is expressed in the periplasm, pMal-p2 from New England Biolabs, Beverly, Mass., USA (Catalog No. 800-65 S).

To do this, pMal-p2 was digested with Xmn I and Sal I, fractionated by gel electrophoresis, and the vector band was eluted by standard methods and ligated to the PCR fragment.

In this way the sequence of the novel thrombin inhibitor (SEQ ID NO: 6) was fused directly to the 3' end of the bacterial gene for the maltose binding protein (mal E).

The construct was transformed by standard methods into the *E. coli* strain TB1 (New England Biolabs).

Growth of transformed cells, induction with IPTG and workup of the periplasmic fraction, and liberation of the thrombin inhibitor by cleavage with factor Xa were carried out exactly as stated by the manufacturer. The individual steps were analyzed by SDS gel electrophoresis.

The activity of the recombinant thrombin inhibitor in the thrombin inhibition assay was entirely comparable to the natural inhibitor from Ornithodoros moubata.

We claim:

1. An isolated and purified protein with a thrombin-inhibitory action from ticks of the genus Ornithodorus, having the following characteristics: an isoelectric point at a pH below 3.8, a molecular weight of 8000±1500 Dalton, determined by SDS polyacrylamide gel electrophoresis, and an N-terminal amino acid sequence represented by the following formula:

Leu-Asn-Val-Leu-Cys-Asn-Asn-Pro-His-Thr-Ala-Asp-Cys-Asn-Asn-Asp-Ala-Gln-Val-Asp    (SEQ ID NO: 11).

2. The protein of claim 1, wherein said protein consists of an amino-acid sequence represented by the formula shown in SEQ ID NO: 7.

3. An isolated DNA coding for the protein of claim 1.

4. The DNA of claim 3 comprising at least one base sequence selected from the group consisting of a base sequence represented by the formula shown in SEQ ID NO: 6, and a base sequence complementary to said base sequence.

5. An expression vector characterized in that it comprises the DNA sequence of claim 3.

6. A method of treating thrombosis or arterial reocclusion, which comprises administering to a patient an effective amount of the protein of claim 1.

* * * * *